Figure 1:
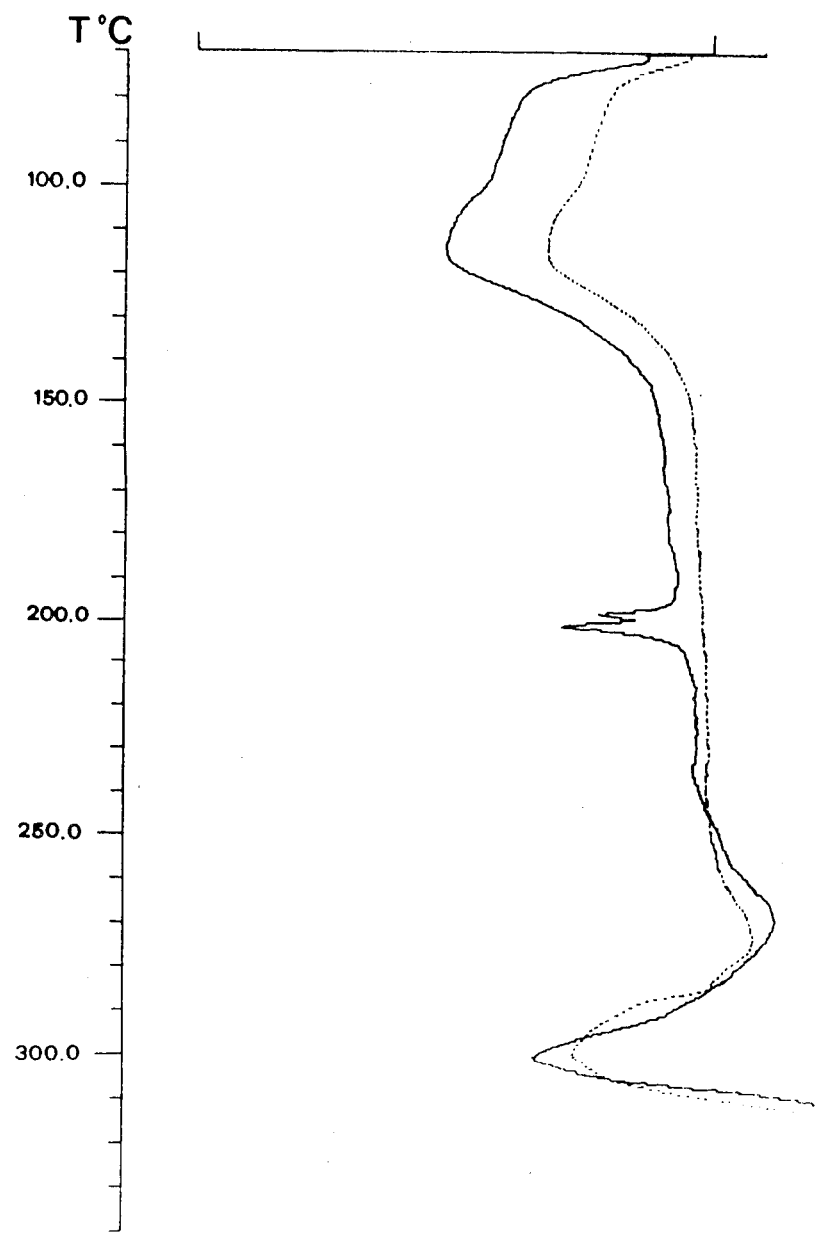

United States Patent [19]

Chiesi et al.

[11] Patent Number: 4,603,123

[45] Date of Patent: Jul. 29, 1986

[54] COMPOUNDS HAVING ANTIINFLAMMATORY ACTIVITY, OBTAINED BY COMPLEXATION OF PIROXICAN WITH β-CYCLODEXTRIN, AND PHARMACEUTICAL COMPOSITIONS CONTAINING THEM

[75] Inventors: Paolo Chiesi; Vittorino Servadio, both of Parma, Italy

[73] Assignee: Chiesi Farmaceutici, S.p.A., Parma, Italy

[21] Appl. No.: 670,979

[22] Filed: Nov. 13, 1984

[30] Foreign Application Priority Data

Feb. 22, 1984 [IT] Italy .................. 19735 A/84

[51] Int. Cl.$^4$ ............................................. A61K 31/73
[52] U.S. Cl. ...................................... 514/58; 536/46; 536/103
[58] Field of Search .............. 424/180, 361; 536/103; 336/46; 514/23, 58

[56] References Cited

U.S. PATENT DOCUMENTS

| | | | |
|---|---|---|---|
| 3,969,338 | 8/1976 | Staron | 260/123.5 |
| 4,365,061 | 12/1982 | Szejtle et al. | 536/103 |
| 4,380,626 | 4/1983 | Szejtle et al. | 536/103 |
| 4,478,995 | 10/1984 | Shinoda et al. | 536/46 |

*Primary Examiner*—Johnnie R. Brown
*Assistant Examiner*—Elli Peselev
*Attorney, Agent, or Firm*—Bucknam and Archer

[57] ABSTRACT

New inclusion compounds of 4-hydroxy-2-methyl-N-2-pyridyl-2H-1,2-benzothiazine-3-carboxyamide-1,1-dioxide with α, β or γ cyclodextrins, obtained by reaction of said cyclodextrins and said 4-hydroxy-2-methyl-N-2-pyridyl-2H-1,2-benzothiazine-3-carboxyamide-1,1-dioxide in aqueous or water/organic solutions are described. The ratio between 4-hydroxy-2-methyl-N-2-pyridyl-2H-1,2-benzothiazine-1,1-dioxide and the cyclodextrins is comprised between 1:10 and 1:1; preferably, it is about 1:2.5.

The compounds of the invention possess high antiinflammatory and analgesic activities, together with a considerably reduced gastrolesive action.

7 Claims, 1 Drawing Figure

COMPOUNDS HAVING ANTIINFLAMMATORY ACTIVITY, OBTAINED BY COMPLEXATION OF PIROXICAN WITH β-CYCLODEXTRIN, AND PHARMACEUTICAL COMPOSITIONS CONTAINING THEM

The present invention refers to new compounds obtained by complexation of 4-hydroxy-2-methyl-N-2-pyridyl-2H-1,2-benzothiazine-3-carboxamide-1,1-dioxide (hereinafter referred to as piroxicam) with α-, β- or γ-type cyclodextrins.

Piroxicam is a compound belonging to the class of the Non Steroidal AntiInflammatory drugs (NSAI) which, thanks to its remarkable analgesic and antiphlogistic activity, is effectively employed in the treatment of arthro-rheumatic diseases. On the other hand, piroxicam is responsible of lesive effects on the gastrointestinal mucosa, though at a lower extent with respect to other drugs of the same therapeutical class widely employed in the clinical praxis.

In addition, piroxicam is practically insoluble in water, and this may represent a limiting factor for an optimal employment of the substance.

It has now been found, and this is the object of the present invention, that piroxicam can advantageously be complexed by inclusion into α-, β- or γ-type cyclodextrins.

The cyclodextrins are natural cyclic compounds consisting of 6(α), 7(β) or 8(γ) (1→4) D-glucopyranosidic units.

The so obtained complex possesses a high solubility, is rapidly absorbed and is better tolerated. In this complex, piroxicam and the cyclodextrins may be present in ratios comprised between 1:1 and 1:10, preferably 1:2.5.

The preparation of the compound can be carried out in different ways:

(a) piroxicam is directly dissolved in an aqueous solution of the selected cyclodextrin, from which the complex separates by crystallization;

(b) piroxicam is dissolved in an organic medium, the organic solution is mixed under stirring with an aqueous solution of the selected cyclodextrin, and the obtained complex is finally separated by crystallization;

(c) the compounds are dissolved under stirring in a water/ammonia solution, and the complex is subsequently separated by drying up;

(d) the compounds are dissolved under stirring in a hot water/ammonia solution, and the complex is subsequently separated by freeze-drying or atomization in air stream.

The compound obtained by this last procedure seems to display more favorable biological properties.

The following examples are only given with the purpose of better illustrating the invention, but in no way they must be construed as a limitation of the scopes of the invention itself.

EXAMPLE 1

50 Milligrams (0.15 mmoles) of piroxicam and 426 mg (0.375 mmoles) of β-cyclodextrin were dissolved in 100 ml of water at 60° C. After stirring for three hours at room temperature and cooling to 3° C., the product separated by crystallization.

EXAMPLE 2

3 Grams (2.643 mmoles) of β-cyclodextrin were dissolved in 100 ml of water, by applying a gentle heating, and the resulting solution was added with a solution of 352.11 mg (1.06 mmoles) of piroxicam in 50 ml of an organic, water immixable solvent, e.g. ethyl acetate. After shaking for 12 hours at room temperature and cooling to 3° C., again under shaking, a precipitate was collected, washed with ethyl acetate and dried in vacuo at 40° C.

EXAMPLE 3

1.3 Grams (3.92 mmoles) of piroxicam and 11.18 g (9.85 mmoles) of β-cyclodextrin were poured under stirring into 780 ml of water. The resulting solution was subsequently added with 26 ml of aqueous 30% ammonium hydroxide and the whole was stirred for 3 hours at room temperature. After 48 hours, the solution was evaporated to dryness and the obtained product was further dried under vacuum in oven at 40° C.

EXAMPLE 4

250 Grams (0.220 moles) of β-cyclodextrin were suspended in 1500 ml of water, the suspension was brought to 60° C. under stirring and subsequently added with 29.20 g (0.088 moles) of piroxicam and 50 ml of aqueous 30% ammonium hydroxide. The limpid solution was then poured into a freeze-dryer, precooled to −20° C. After freeze-drying, the product was refined.

EXAMPLE 5

250 Grams (0.220 moles) of β-cyclodextrin were suspended in 1500 ml of water, the suspension was brought to 60° C. under stirring and subsequently added with 29.2 g (0.088 moles) of piroxicam and 50 ml of aqueous 30% ammonium hydroxide. The limpid solution was then dried by atomization in air stream, pH=5.7 (determined on a saturated solution of piroxicam/β-cyclodextrin).

The so obtained product was characterized as follows:

(a) Quantitative determination of piroxicam complezed by the β-cyclodextrin

An amount of complex corresponding to about 10 mg of piroxicam, accurately weighed, was taken up with 1000 ml of 0.1 N NaOH in methanol. The amount of piroxicam in the complex was spectrophotometrically determined on the solution, previously filtered through paper, at 358 nm against 0.1 N NaOH in methanol.

(b) Characterization of the complex by Differential Scanning Calorimetry (D.S.C.)

About 5 mg of the complex piroxicam/β-cyclodextrin, exactly weighed, were analyzed under the following conditions:
starting temperature—70° C.
temperature gradient—10° C./min.
final temperature—350° C.

The typical endothermic peaks of free piroxicam, appearing at about 200° C., must be absent. The results are shown in FIG. 1, in which the D.S.C.-curve of the complex piroxicam/β-cyclodextrin (Drawing A) is compared with that of a physical mixture of piroxicam and β-cyclodextrin (Drawing B).

The solubility characteristics of the complex piroxicam/β-cyclodextrin (1:2.5), obtained by the freeze-drying method, were determined with the aid of a "Dissolution Tester" apparatus, in agreement with the specification of the U.S. Pharmacopoeia, 20th. edition, at a speed of 100 r.p.m. and at the temperature of 25° C.

EXAMPLE 6

7.5 Grams of piroxicam/β-cyclodextrin were poured into 150 ml of water at 25° C. under stirring. At predetermined time intervals, samples of 5 ml of suspension were collected and filtered through 0.2μ. Milliliters of the filtrate were diluted 1 to 500 with 0.1 N NaOH in methanol immediately after the filtration. The whole was again filtered through paper.

The amount of piroxicam in the solution was spectrophotometrically determined at 358 nm against a solution of 0.1 N NaOH in methanol.

After 30 minutes since the beginning of the dissolution test, the percent concentration of piroxicam complexed with β-cyclodextrin was 0.0463 (expressed as g/100 ml) whereas, under the same experimental conditions and at the same time, the percent concentration of piroxicam alone was 0.0111 (expressed as g/100 ml).

Accordingly, the solubility of piroxicam in the complex with β-cyclodextrin is 4 times higher than that of piroxicam as such.

The complex piroxicam/β-cyclodextrin 1:2.5 obtained by the freeze-drying procedure was investigated with respect to its pharmaco-toxicological properties in comparison with piroxicam as such.

All the indicated dosages are expressed as dosages of active principle (piroxicam).

Antiinflammatory activity

The antiinflammatory activity was determined by means of the carrageenin induced oedema test, according to the methodology reported by C. A. Winter et al in Proc. Soc. Exptl. Biol. Med. 111, 544, 1962. As the test animals, male Crl:CD(SD) rats, weighing 150–170 g, were employed. The animals were housed under standard conditions and fastened for 18 hours before the beginning of the experiment. Water was available ad libitum.

The activity of the compounds to be tested, administered at different dosages by oral route, was determined by measuring the inhibition of the oedema induced in the rat paw by the injection of 0.1 ml of a 1% carrageenin suspension in physiological solution into the subplantar aponeurosis of the right hind paw.

The obtained results were expressed both as $ED_{50}$ values, determined in correspondence of the activity peak on the regression line log. of the dosage-% inhibition of the oedema, and as $ED_{30}$ values, calculated on the regression lines log. of the dosage-% inhibition of the oedema over the controls, determined as the mean value of AUC (area under Curve representing the development of the paw volume in the time).

In addition, it was determined the kinetic of the activity of the two formulations under investigation, by calculating the $ED_{30}$ values at 2, 3, 4 and 6 hours since the carrageenin injection.

The results are reported in Tables 1 and 2.

TABLE 1

Antiinflammatory activity determined by the carrageenin induced oedema test in rats. Comparison between the complex piroxicam/β-cyclodextrin and piroxicam.

| Compound | Peak Activity $ED_{50}$ (mg/kg) | PR | Activity on AUC $ED_{30}$ (mg/kg) | PR |
|---|---|---|---|---|
| Complex piroxicam/β-cyclodextrin | 1.1 | 2.1 | 1.2 | 2.1 |
| Piroxicam | 2.3 | 1 | 2.5 | 1 |

P.R. = Potency ratio over piroxicam (Piroxicam = 1)

TABLE 2

Antiinflammatory activity determined by the carrageenin induced oedema test in rats. Kinetic of the activity of the compounds, expressed as $ED_{30}$, at different time intervals since the carrageenin injection

| Compound | $ED_{30}$ (mg/kg) at different time intervals | | | |
|---|---|---|---|---|
| | 2 h | 3 h | 4 h | 6 h |
| Complex piroxicam/β-cyclodextrin | 0.38 | 0.76 | 1.5 | 11.9 |
| Piroxicam | 0.60 | 1.6 | 3.1 | 9.7 |
| Potency ratio (piroxicam = 1) | 1.6 | 2.1 | 2.1 | 0.82 |

Gastrolesive Action

The gastrolesive action was tested on rats fastened for 18 hours, through macroscopical examination of the gastric mucosa, 5 hours after the administration of the substances under investigation. For each treatment, the regression lines log. of the dosage-mm of ulceration (single values for each animal) were determined. These lines allowed to calculate, for each compound, the $UD_0$ values i.e., the maximum dosages at which no lesions are observed.

Finally, it was also determined the therapeutic index of the new compound piroxicam/β-cyclodextrin, in comparison with piroxicam. Said index was expressed as the ratio $UD_0/ED_{30}$ wherein $UD_0$ and $ED_{30}$ are as above defined.

The obtained results are reported in the following Table 3.

TABLE 3

Determination of the absolute and relative therapeutic indexes of the complex piroxicam/β-cyclodextrin in comparison with piroxicam, expressed as the $UD_0/ED_{30}$ ratio

| Compound | Antiinflammatory activity $ED_{30}$ (mg/kg) | Gastrolesive activity $UD_0$ (mg/kg) | Absolute therapeutic index | Relative therapeutic index |
|---|---|---|---|---|
| Complex piroxicam/β-cyclodextrin | 1.2 | 1.4 | 1.17 | 2.65 |
| Piroxicam | 2.5 | 1.1 | 0.44 | 1 |

From the examination of the results, it can be inferred that, in comparison with piroxicam alone, the complex piroxicam/β-cyclodextrin shows a marked increase of activity, together with an improved gastric tolerability.

The ratio between these two values i.e., the therapeutic index, proves to be particularly advantageous for the complex, being 2.65 times higher than that of the active ingredient as such, conventionally equal to 1.

Bioavailability and pharmacokinetic

For these investigations, male New Zealand White rabbits, weighing 2.5-3.0 kg were employed. The animals were kept at constant temperature and fastened for the 17 hours preceeding the experiments. Water was given ad libitum.

The oral administration of the compounds to be tested was performed by oesophageal gavage, as a suspension in carboxymethylcellulose (CMC); the compounds were administered at a dosage corresponding to 10 mg/kg of active ingredient, at the constant volume of 10 ml/kg.

The determination of the plasma levels of the active principle, at the different times since the administration, was carried out by High Pressure Liquid Chromatography (HPLC). The obtained results are reported in Table 4.

The complex piroxicam/$\beta$-cyclodextrin is able to induce high plasma levels of active ingredient, significantly higher than those observed after the administration of said active ingredient as such, even at 15, 30 and 60 minutes after its administration: it derives, therefore, that the AUC (Area Under (the) Curve plasma levels/times) of the complex piroxicam/$\beta$-cyclodextrin, which refers to the first 2 hours after the treatment and is equal to 29.59∓3.38 mcgml$^{-1}$.h($\overline{X}\pm$S.E.), is significantly greater—55% wider—than that of the active ingredient as such.

Moreover, the maximum concentration peak appears very soon (in the first 30 minutes since the beginning of the treatment), and is considerably higher than that obtained after administration of piroxicam as such.

On the other hand, the global bioavailability during the 24 hours remains more or less unchanged: this is due to the fact that, in this animal species (rabbit), piroxicam itself displays indeed an almost complete bioavailability.

In another animal species i.e., the dog, in which the bioavailability patterns, particularly with reference to piroxicam, are somewhat similar to those observed in men, the behavior of the complex piroxicam/$\beta$-cyclodextrin proved to be considerably different.

Four Beagle dogs, weighing 8-10.5 kg, were employed as the test animals. The dogs were kept at constant temperature and fastened at least for 17 hours before the beginning of the experiment. Water was available ad libitum.

The two substances to be investigated were orally administered at a dosage corresponding to 10 mg/kg of active ingredient, according to a crossover scheme. The determination of the plasma concentrations of the active ingredient, at a different time intervals since the administration, was carried out by High Pressure Liquid Chromatography (HPLC).

The obtained result are reported in Table 5.

From the comparison of the plasma kinetics, it appears evident that, as far as the absorption is concerned, the two substances differ both from the qualitative and the quantitative standpoint; in fact, the plasma levels of the complexed form are extremely high (about 80% of the maximum values), and appear almost immediately (15 minutes after the administration); contemporaneously, the analysis of the AUCs in the time interval 0-2 hr makes evident a significant difference ($p<0.005$) in the two treatments. Also the differences of the plasma concentrations at almost all of the observation times and, consequently, the AUCs in the time interval 0-72 hr, are absolutely significant. In view of these results, it can be concluded that, in the dog, the formation of an inclusion complex between piroxicam and $\beta$-cyclodextrin is capable of inducing not only an accelerated absorption, but also a global increase in bioavailability (about 40%). It must be pointed out that an immediate onset of therapeutically useful plasma levels is of primary importance for the analgesic action, which must be rapid and effective.

TABLE 4

Plasma kinetics of piroxicam in the rabbit, after oral administration of equivalent dosages in active ingredient (10 mg/kg) of piroxicam and piroxicam/$\beta$-cyclodextrin (1:2.5).

| Compounds | No of animals | | Plasma concentrations ($\mu$gml$^{-1}$) of piroxicam ($\overline{X}\pm$ S.E.) at the different times (h) after the administration | | | | | | | AUC (0-24 h) $\mu$gml$^{-1}\cdot$h | AUC (0-2 h) $\mu$gml$^{-1}\cdot$h | $C_{max}$ $\mu$gml$^{-1}$ | $T_{max}$ h |
|---|---|---|---|---|---|---|---|---|---|---|---|---|---|
| | | | 0.25 | 0.50 | 1 | 2 | 4 | 8 | 24 | | | | |
| Piroxicam | 6 | $\overline{X}\pm$ | — | 4.3 | 7.4 | 10.9 | 10.1 | 6.5 | 0.3 | 121.28 | 13.17 | 11.7 | 2.3 |
| | | S.E. | — | 0.9 | 1.1 | 1.8 | 2.2 | 0.9 | 0.1 | 18.22 | 2.00 | 1.9 | |
| Complex piroxicam/$\beta$-cyclodextrin | 5 | $\overline{X}\pm$ | 15.1 | 17.3 | 16.6 | 13.8 | 8.5 | 3.8 | 0.9 | 114.53 | 29.59 | 18.4 | 0.6 |
| | | S.E. | 2.9 | 1.5 | 2.0 | 1.6 | 0.8 | 0.9 | 0.5 | 12.96 | 3.38 | 2.0 | |
| p(*) | | | — | <0.001 | <0.005 | N.S. | N.S. | N.S. | N.S. | N.S. | <0.005 | <0.05 | — |

(*)Statistically significant difference (Student t-test for independent data) with respect to the corresponding values obtained after administration of prioxicam

TABLE 5

Plasma kinetics of piroxicam in the dog, after oral administration of equivalent dosages in active ingredient (10 mg/kg) of piroxicam and piroxicam/$\beta$-cyclodextrin (1:2.5).

| Compounds | No of animals | | Plasma concentrations ($\mu$gml$^{-1}$) of piroxicam ($\overline{X}\pm$ S.E.) at the different times (h) after the administration | | | | | | | | | AUC (0-72 h) $\mu$gml$^{-1}\cdot$h | AUC (0-2 h) $\mu$gml$^{-1}\cdot$h | $C_{max}$ $\mu$gml$^{-1}$ | $T_{max}$ h |
|---|---|---|---|---|---|---|---|---|---|---|---|---|---|---|---|
| | | | 0.25 | 0.50 | 1 | 2 | 4 | 8 | 24 | 48 | 72 | | | | |
| Piroxicam | 4 | $\overline{X}\pm$ | 1.0 | 2.8 | 12.7 | 19.4 | 18.9 | 14.2 | 11.5 | 9.2 | 3.0 | 723.64 | 20.44 | 20.0 | 1.8 |
| | | S.E. | 0.4 | 1.0 | 2.6 | 0.6 | 0.2 | 0.3 | 0.7 | 0.4 | 0.3 | 20.33 | 2.18 | 0.2 | — |
| Complex piroxicam/$\beta$-cyclodextrin | 4 | $\overline{X}\pm$ | 26.2 | 30.7 | 34.8 | 34.8 | 28.7 | 28.6 | 18.5 | 11.0 | 5.5 | 1167.53 | 61.53 | 35.7 | 1.5 |
| | | S.E. | 3.4 | 3.7 | 3.5 | 2.3 | 3.2 | 2.9 | 2.2 | 1.2 | 1.1 | 97.45 | 5.43 | 2.9 | — |

TABLE 5-continued

| | | Plasma kinetics of piroxicam in the dog, after oral administration of equivalent dosages in active ingredient (10 mg/kg) of piroxicam and piroxicam/β-cyclodextrin (1:2.5). | | | | | | | | | | | |
|---|---|---|---|---|---|---|---|---|---|---|---|---|---|
| Compounds | No of animals | Plasma concentrations ($\mu gml^{-1}$) of piroxicam ($\overline{X} \pm$ S.E.) at the different times (h) after the administration | | | | | | | | AUC (0-72 h) $\mu gml^{-1} \cdot h$ | AUC (0-2 h) $\mu gml^{-1} \cdot h$ | $C_{max}$ $\mu gml^{-1}$ | $T_{max}$ h |
| | | 0.25 | 0.50 | 1 | 2 | 4 | 8 | 24 | 48 | 72 | | | |
| p(*) | | <0.005 | <0.01 | <0.005 | <0.005 | N.S. | <0.025 | N.S. | N.S. | <0.05 | <0.025 | <0.005 | <0.025 | — |

(*)Statistically significant difference (Student t-test for paired data) with respect to the corresponding values obtained after administration of piroxicam

Kinetic of the analgesic activity

The kinetic of the oral analgesic activity of the complex piroxicam/β-cyclodextrin in comparison with piroxicam was investigated by means of the phenylquinone induced writhing test, by evaluating the degree of protection displayed by the tested substances against a characteristic syndrome (writhing), induced upon intraperitoneal injection of 10 ml per kg of body weight of an aqueous solution of phenylquinone (0.02% in 5% aqueous ethanol). The employed experimental model is a slight modification of that described by Siegmund, J. Pharm. Exptl. Ther., 119, 184, 1957.

Female NMRI mice, housed under standard conditions, fastened for 18 hours, were employed as the test animals. Water was available ad libitum.

The compounds under study were orally administered by oesophageal gavage, suspended in an aqueous solution containing 0.5% of carboxymethylcellulose, at a concentration corresponding to 0.5 mg/kg of active substance (piroxicam).

The obtained results again confirm the noteworthy increase of the absorption rate of piroxicam, when complexed by inclusion into the β-cyclodextrin, in comparison with the active principle as such, following the oral administration. In fact, even 5 minutes after the administration, it was observed the 99% of the maximum evidenced inhibition for the complex piroxicam/β-cyclodextrin, whereas that observed for piroxicam as such at the same time was 78%.

The activity peak which, in the case of piroxicam/β-cyclodextrin, is just that monitored after 5 minutes, appears only after 20 minutes in the case of piroxicam as such.

All of these properties, namely the improved bioavailability, the increase in activity as well as its rapid onset, and the improved tolerability bestow on the compound of the invention a particular therapeutic interest.

The present invention also refers to pharmaceutical compositions containing, as the active ingredient, piroxicam complexed by inclusion into cyclodextrins in the above defined ratios, in admixture with pharmaceutically acceptable excipients.

The compositions can be administered by oral or rectal route, respectively in the form of capsules, tablets, bags, syrups, solutions and the like, or suppositories.

In the preparation of pharmaceutical formulations in dosage unit form suitable for the oral administration, the active ingredient can be admixed with a solid pulverized excipient such as, for instance, lactose, saccharose, sorbitol, mannitol, potato-corn, or maize starch or amylopectin, a cellulose or gelatin derivative, and may also contain lubricants, e.g. talc, magnesium or calcium stearate, polyethyleneglycol or silica.

The tablets can be coated in different ways, according to methods well known from the pharmaceutical practice. Hard gelatin capsules may contain granulates of the active ingredient in admixture with solid pulverized excipients such as, for instance, lactose, saccharose, sorbitol, mannitol, starches (as above indicated), cellulose or gelatin derivatives, and may also contain stearic acid, or magnesium stearate or talc.

Unit dosage forms for the rectal administration are generally represented by suppositories, and contain the active ingredient in admixture with a neutral fatty base (for instance, glycerides of fatty acids), or with water soluble or autoemulsifiable excipients (e.g., mixtures of polyethyleneglycols). The unit dosage for the above illustrated formulations may vary from about 10 to about 50 mg of active ingredient, and is preferably given in a single administration on a daily basis.

Some representative, but not limitative, pharmaceutical formulations according to the invention are hereinbelow reported for illustrative purposes.

Tablets

Piroxicam/β-cyclodextrin (1:2.5) corresponding to 20 mg of piroxicam)—mg 191.2
Microcrystalline cellulose or starch—mg 80
Sodium carboxymethylstarch—mg 8
Lactose or calcium phosphate—mg 108
Magnesium stearate—mg 2.8

Effervescent tablets

Piroxicam/β-cyclodextrin (1:2.5) (corresponding to 20 mg of piroxicam)—mg 191.2
Glycine sodium carbonate—mg 500
Citric acid—mg 500
Sodium benzoate—mg 40
Polyethyleneglycol 6000—mg 15
Monoammonium glycyrrhizinate—mg 30
Mint flavor—mg 5
Saccharose—mg 718.8

Bags

Piroxocam/β-cyclodextrin (1:2.5) (corresponding to 20 mg of piroxicam)—mg 191.2
Silica gel—mg 10
Sodium saccharine—mg 10
Monoammonium glycyrrhizinate—mg 30
Mint flavor—mg 5
Saccharose (mannitol, sorbitol, xylitol, fructose or mixture thereof)—mg 4753.8

Suppositories

Piroxicam/β-cyclodextrin (1:2.5) (corresponding to 20 mg of piroxicam)—mg 191.2
Semisynthetic solid glycerides to mg 1600.

We claim:

1. The inclusion complex of piroxicam with α,β- or γ cyclodextrin, in the ratio between 1:1 and 1:10 of piroxicam and said cyclodextrin respectively.

2. The inclusion complex according to claim 1, wherein the piroxicam/cyclodextrin ratio is 1:2.5.

3. The inclusion complex according to claim 1, wherein the cyclodextrin is β-cyclodextrin.

4. A pharmaceutical composition useful as an analgesic, in unit dosage form comprising an effective amount of the inclusion complex of piroxicam and beta-cyclodextrin wherein said piroxicam and said cyclodextrin are in the ratio between 1:1 and 1:10 respectively and at least one pharmaceutically acceptable carrier.

5. A pharmaceutical composition according to claim 4 in the form of tablets, compresses, sachets, suppositories, suited for oral or rectal administration, containing from 10 to 50 mgs of said inclusion complex per unit dosage.

6. A pharmaceutical composition having antiinflammatory activity for oral or rectal administration, in the form of tablets, capsules, sachets or suppositories containing an effective amount of an inclusion complex of piroxicam and beta-cyclodextrin wherein said piroxicam and said cyclodextrin are in the ratio between 1:1 and 1:10 respectively and at least one pharmaceutically acceptable carrier.

7. A pharmaceutical composition according to claim 6, containing from 10 to 50 mg of said inclusion complex per unit dosage.

* * * * *